United States Patent [19]

Matney

[11] Patent Number: 4,763,930

[45] Date of Patent: Aug. 16, 1988

[54] TRANSPARENT GUMMED LABEL HAVING SEE THROUGH INDICIA AND OPAQUE UNIVERSAL PRODUCT CODE BAR AND NUMERICAL INDICIA AT A SIDE THEREOF ON SMALL NAIL POLISH BOTTLES

[76] Inventor: Arthur Matney, 4014 First Ave., Brooklyn, N.Y. 11232

[21] Appl. No.: 47,571

[22] Filed: May 5, 1987

Related U.S. Application Data

[63] Continuation of Ser. No. 751,898, Jul. 5, 1985, abandoned.

[51] Int. Cl.[4] .......................... B42D 15/00; A44C 3/00; G09F 19/00; A61F 13/02

[52] U.S. Cl. .......................... 283/81; 40/310; 40/638; 428/40

[58] Field of Search .............. 283/79, 80, 81; 40/2 R, 40/310, 615 A; 428/40, 353; 206/67, 56; 156/281; 272/8

[56] References Cited

U.S. PATENT DOCUMENTS

| | | | |
|---|---|---|---|
| 2,262,492 | 11/1941 | Farrell | 40/2 |
| 2,422,314 | 6/1947 | Rheinstrom | 206/47 |
| 2,580,305 | 12/1951 | Kremer | 272/8 |
| 2,613,168 | 10/1952 | Tottem, Jr. | 154/46 |
| 2,654,170 | 10/1953 | Nestor | 40/4 |
| 3,245,857 | 4/1966 | Rutledge | 156/281 |
| 3,420,364 | 1/1969 | Kennedy, Jr. | 206/56 |
| 3,515,630 | 6/1970 | Columbus et al. | 161/245 |
| 3,543,241 | 11/1970 | Leuck | 340/172.5 |
| 3,702,511 | 11/1972 | Miller | 283/81 |
| 3,711,683 | 1/1973 | Hamisch, Sr. | 40/2 R |
| 3,857,803 | 12/1974 | Shenfeld | 40/310 |
| 3,874,893 | 4/1975 | Cherrin | 40/2 R |
| 4,027,426 | 6/1977 | Wallding et al. | 40/310 |
| 4,061,808 | 12/1977 | Sato | 40/2 R |
| 4,128,954 | 12/1978 | White | 283/81 |
| 4,204,639 | 5/1980 | Barber et al. | 40/2 R |
| 4,273,816 | 6/1981 | Tollette | 40/615 |
| 4,324,058 | 4/1982 | Sherwick et al. | 40/310 |
| 4,379,805 | 4/1983 | Downing | 428/353 |
| 4,505,497 | 3/1985 | Katzman | 283/81 |
| 4,661,189 | 4/1987 | Voy et al. | 428/40 |
| 4,682,433 | 7/1987 | Stilling | 283/81 |

*Primary Examiner*—E. R. Kazenske
*Assistant Examiner*—Paul M. Heyrana, Sr.
*Attorney, Agent, or Firm*—Hoffmann & Baron

[57] ABSTRACT

This invention relates to a transparent gummed label for small nail polish glass containers fitted with a cap-applicator, the label being formed of a pre-cut clear cellulose acetate sheet having translucent light colored printing over a major proportion of the back and the bar code printed on the front of the sheet. Specifically the left back side of the sheet is printed with a first light colored material identifying the supplier and the shade of the nail polish contents. Immediately adjacent thereto but on the front side there is a second printing of a white opaque background located on the right side which is a minor portion of the sheet and which is then overprinted with the opaque black Universal Product Code Bar Code and then with the Universal Product Numbers adjacent the Bar Code. The back side of the sheet is then coated with a clear pressure sensitive adhesive so that the label is then applied to a small glass container (½ fluid ounce) for nail polish. The transparent light colored indicia on the back side identify the manufacturer supplier, the shade of nail polish, the fluid contents (½ fluid oz. or 15 ml) and give instructions to shake well before removing the cap. The consumer can match the shade to any desired color and readily sees through the label which is of a significantly large size in relation to the size of the glass container. The label facilitates consumer selection of any shade desired in an offering of about 75-80 nail polish colors.

26 Claims, 1 Drawing Sheet

TRANSPARENT GUMMED LABEL HAVING SEE THROUGH INDICIA AND OPAQUE UNIVERSAL PRODUCT CODE BAR AND NUMERICAL INDICIA AT A SIDE THEREOF ON SMALL NAIL POLISH BOTTLES

This is a continuation of co-pending application Ser. No. 751,898, filed on July 5, 1985, now abandoned.

BACKGROUND OF THE INVENTION

1. Field of the Invention

The invention lies in the field of back printed transparent gummed cellulose acetate labels applied to small containers of nail polish for the purpose of identifying the manufacturer, the product, and the shade or tint of the nail polish in glass containers of small size, e.g. about ½ fluid oz. or 15 ml and in which a Universal Product Code comprising the Bar Code and numbers are separately printed in an opaque front portion of the label. The instructions to the user for shaking the contents are also printed in a translucent or transparent see through light color on the back of the label.

2. Description of the Prior Art

Heat resistant and solvent resistant transparent labels having an ink graphic layer on the back side thereof are disclosed in Downing et al, U.S. Pat. No. 4,379,805. A construction is shown which includes a release liner which is peeled away to apply the label. An opaque flood coating is applied over the heat resistant transparent film to create a white opaque layer over the entire label, for adaptation to a harsh industrial atmosphere when used on aircraft exposed to jet fuel.

Labels which use special adhesives for reusable bottles are widely used in the soft drink industry and for beer. Examples are Totten, Jr., U.S. Pat. No. 2,613,168, Shenfeld, U.S. Pat. No. 3,857,803 and Wallding et al, U.S. Pat. No. 4,027,425. These labels are of the type which disintegrate in the alkaline washing solution used with the glass soft drink bottles or beer bottles so the label can be readily eliminated and new labels applied. In all of these patents special adhesive or special label constructions the printing which may be gravure printing as in Totten, is generally applied to the opposite side in relation to the side to which the adhesive is applied. For example, see Column 3, lines 20–26 in Totten. Hence in all cases the indicia or printing to identify the source and contents are generally applied on the front surface.

In Farrell, U.S. Pat. No. 2,262,492, ordinary ink is used to print on the top imprint and fluorescent ink is used to print on the back. The requirement for identification of the fluorescent ink in Farrell is to provide ultraviolet light in order to view the fluorescent printed character which is absent from the present invention.

In Kremer, U.S. Pat. No. 2,500,305 the coating on the label is one which is selected to cooperate with the dye and liquid contents within the bottle and an image is projected on the label to create an optical effect. This effect is totally different from seeing through a transparent label as in the present invention.

Heat sensitive adhesives have been used in applying labels to glass bottles and these are taught in Rutledge U.S. Pat. No. 3,245,857.

ADDITIONAL PRIOR ART SHOWING PRESSURE SENSITIVE ADHESIVES AND UNIVERSAL PRODUCT BAR CODE

Pressure sensitive adhesives are well known for glass bottles and plastic containers and used for applying labels to such plastic containers as PVC containers and polystyrene containers as disclosed in Columbus et al, U.S. Pat. No. 3,515,630.

Pressure sensitive adhesive labels are used in combination with a peelable backing layer construction similar to the release liner layer of the above-mentioned Downing, et al U.S. Pat. No. 4,379,805 and another example which is similar to U.S. Pat. No. 4,379,805 is Kennedy, Jr., U.S. Pat. No. 3,420,364, granted Jan. 7, 1969, this patent showing a backing strip having perforations some of which are placed between adjacent labels on the backing strip.

It is common to have different opaque portions on gummed labels used for preparing index tapes used on flat files or magnetic tape cartridges or casettes and the like and a gummed label having two opaque portions, one portion of which is color coded and the other portion of which is bar coded with numerical indicia is shown in Barber et al, U.S. Pat. No. 4,204,639. This opaque label is not adapted for use on a bottle but instead is specifically designed for use on large flat files which are part of a larger filing system.

Hamisch, Sr., U.S. Pat. No. 3,711,683 discloses a gummed label bearing the bar code and price data which is used as a paste over label to show a new price on an existing label having the same data. The price data on the paste over label is colored red to reflect a price change and the example is given in the drawings of a price of $4.59 which is shown on tag 17.

Conventional apparatus used to read the bar code is well known in the art and an example is shown in Leuck U.S. Pat. No. 3,543,241. All of the bar coded labels used in the file systems in the prior art have been used in combination with opaque color coding and in no case am I aware of any pressure sensitive adhesive label being constructed to provide a see through transparent portion constituting the major product identifying portion of the label together with an opaque portion bearing the bar code..

SUMMARY OF THE INVENTION

This invention relates to a transparent gummed cellulose acetate label applied to small nail polish glass containers fitted with a cap applicator. There is no cosmetic product of which I am aware which has developed a greater number of colors and shades in response to customer demand than the nail polish compositions which have been universally marketed in glass containers containing a very small amount of the nail polish liquid material, generally ½ fluid ounce or 15 ml. As a supplier and manufacturer of nail polish to retail outlets I have over the past 20 years increased the variety of colors and shades to maintain a present inventory of about 80 nail polish colors, each internally coded by the manufacturers code number and given an identifying name to help the consumer in making a selection of the color desired for matching to the cosmetics used by that consumer. The pressure sensitive adhesive label which I have used throughout my manufacturing operations is based upon cellulose acetate sheet material.

In the present invention, the label per se is formed of a pre-cut clear cellulose acetate sheet having translucent light colored printing over a major proportion of the left back side of the sheet identifying the supplier and shade of the nail polish contents and immediately adjacent thereto but on the front side having a white opaque background printed on the remaining right side minor portion of the sheet which is overprinted with the opaque black Universal Product Code Bar Code and also overprinted with the Universal Product Numbers adjacent the bar code so that when the back side of the sheet is coated with a clear pressure sensitive adhesive the label can then be applied to a small glass container for nail polish. The printing operation which is carried out on the back surface of the pre-cut cellulose acetate sheet and on the left side is a first and separate printing operation from that which is carried out on the front side of the sheet and on the right side thereof. The design of the present transparent label portion is such that the essential product and source information is transmitted to the user or consumer. The transparent light colored indicia on the underside of the transparent or clear cellulose acetate sheet should identify the manufacturer supplier, the shade of nail polish, the fluid contents (½ fluid oz. or 15 ml) and give instructions to shake well before removing the cap. The consumer can match the shade to the designated color and readily see through the label which is of a relatively large size in relation to the glass container.

The product code bar and numbers are in the size required for being registered on the conventional electronic Universal Product Code scanners and an example of such scanner is found in the patent to Leuck, U.S. Pat. No. 3,543,241. The label facilitates consumer selection of a desired shade in an offering of about 75–80 nail polish colors offered by the supplier yet permits ringing up or checking the article by the new electronic registers having binary code scanning equipment.

An essential feature of the first separate printing operation is that it is carried out on the back surface in a first area constituting the major portion of the pre-cut cellulose sheet and in a front surface area immediately adjacent to the edge boundary of the inner edge of printing. This edge serves for the alignment of the front double printing operation which is needed to provide the Universal Product Bar Code in black on a white opaque background. It is necessary to maintain a sharp line of demarcation or boundary line between the inner side edge of the back indicia and the inner front edge of the top bar code indicia. There is no overlap between the first and second printings across this boundary line. The result is to provide a very clear white opaque edge at the boundary line defining the background for the front indicia which are overprinted in black and this is an outstanding visual aspect of the front of the label. The white opaque background on the front is in a substantial thickness several times greater than the thickness of the light colored bottom indicia on the back. The second overprinting of the black bar code symbols provides a very sharp contrast in the black bars over the white background. The opaque coatings are applied preferably by double coating the white opaque background in a thickness which is many times greater than the thickness of the product identifying indicia on the left back side of the cellulose acetate sheet which results in creating a translucency or see through character for the product indicia on the left back side of the label with a non see through or complete opacity in the Product Bar Code area and white opaque background at the right side of the front of the label. Obviously the thickness in the bar code and number printed area is greater than in the non-marked areas, e.g. the white opaque areas on the right side of the labels. Accordingly, the overall print thickness is about 3 to 5 times greater on the right side of the label in the opaque printed areas than the left back side of the label where the thinness and light color together permit a see through aspect to view the color of the nail polish contents after the label is applied to the bottle.

DESCRIPTION OF THE PREFERRED EMBODIMENT

Figure 1:
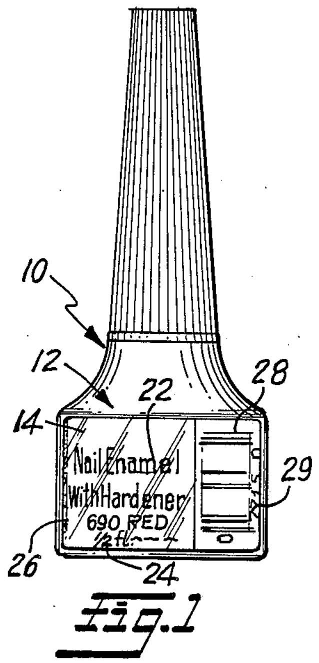
FIG. 1 is a front elevational view of the nail polish bottle with the label adhesively secured thereto.

In FIG. 1 there is shown the adhesive assembly of the novel label 12 adhered to the bottle 10, the bottle 10 being a conventionally shaped glass bottle for nail polish fitted with a screw cap in which there is secured a brush applicator (not shown). The top of the bottle 10 is formed with screw threads in the glass to accommodate the internal threads in the screw cap. The bottle 10 has a squat cylindrical body form as seen in FIG. 1 and the height of the body portion is such that it accommodates the label height to permit the label 12 to be adhesively secured by means of a pressure sensitive adhesive 30 to the bottle 10 with the short dimension of the label 12 constituting the vertical side of the label in relation to the cylindrical height of the bottle and the length of the label 12 being such that it occupies a significant arcuate area of the cylindrical body portion of the bottle 10. In the particular size widely used by the customer, namely: ½ fluid oz. or 15 ml, the label 12 measures about 1 inch in height and about 1 7/16 inches in length. This size label is adapted to fit a bottle size having a cylindrical height slightly larger than one inch or a bottle having a much greater cylindrical height to assure proper fitting of the label to the side.

Figure 2:
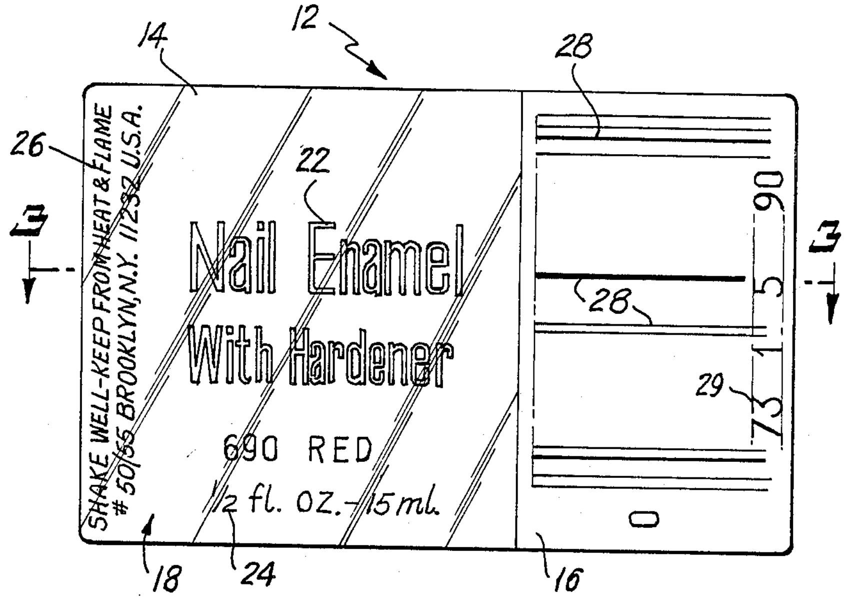
FIG. 2 is an enlarged plan view of the label.

The visual aspect of the label 12 which is presented to the consumer is best seen in FIG. 2 which shows an enlarged form. The product identifying indicia 22 which is seen in FIG. 2 gives the common name for the contents "Nail Enamel With Hardener" is applied by printing to the back side of the base sheet 14 of precut cellulose acetate in the transparent portion of the label 12 and at the left side. The left side of the label 12 comprises additional indicia identifying the manufacturer or company which supplies the product, e.g. nail polish, but the drawing does not indicate any specific manufacturer or company source. A legend 26 at the left side of the label 12 is formed of printed indicia which instructs the customer to "shake well before using" and warns the consumer not to use the product in the presence of any flame or heat because the contents are flammable. The indicia on the product identification side of the label which is the left side, also includes the identification of the color by the indicia "690 Red" as shown in FIG. 2. Also the indicia on the product identification side includes the quantity indicia 24, e.g. $\frac{1}{2}$ fluid oz. or 15 ml.

All of the indicia 22, 24, 26 which are applied to the left major portion of the label 12 on the back side thereof are in a light color, white or buff, ink in a light thickness, e.g. of the order of 013 to about 0.6 mils. As a result of the thin coating and light color the printing on a clear transparent substrate furnished by the pre-cut cellulose acetate sheet 14 permits the contents of the nail enamel of a red color to be fairly visible through the printing and the left side of the label as a see through character which is more pronounced in the non-printed areas than in the printed areas but nevertheless see through throughout.

METHOD OF PRINTING DIE CUT CELLULOSE ACETATE BLANK

Figure 3:
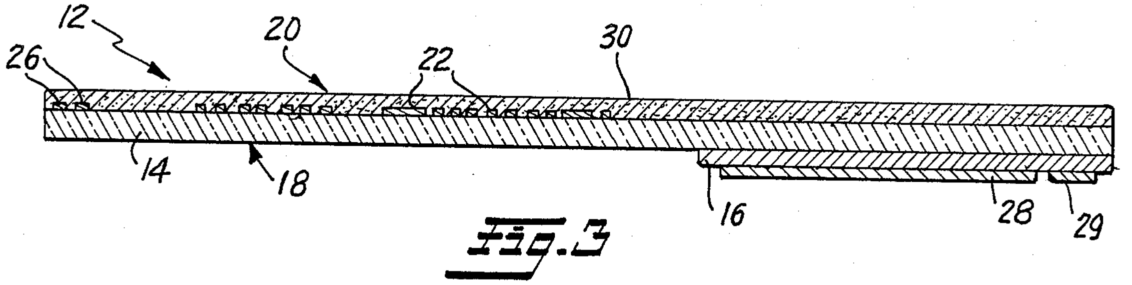
FIG. 3 is a horizontal sectional view along lines 3—3 of FIG. 2.
Figure 4:
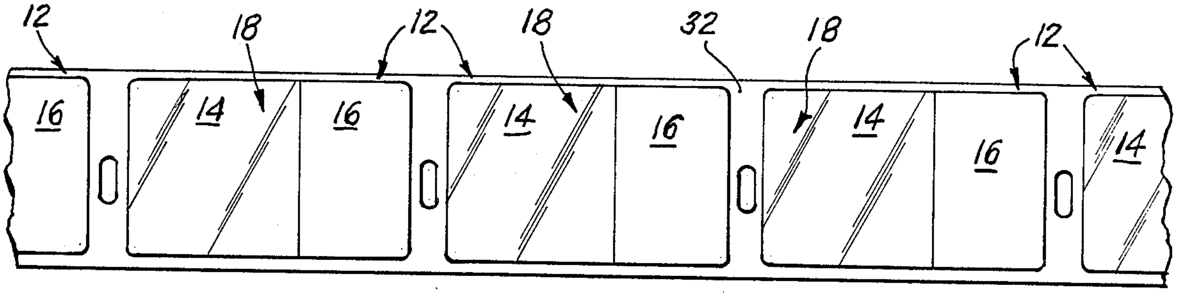
FIG. 4 shows a fragmentary front elevational view of a plurality of labels in a longitudinal sequence mounted on a peelable strip provided with an aperture between the labels to facilitate machine registration of the labels for peeling from the strips and applying to a nail polish bottle.

The cellulose acetate blank 14 of FIGS. 2 and 3 is printed by conventional printing machinery such as gravure printing machinery and flexographic printing machinery in a sequence of printing operation comprising the following steps:

1. Printing the back of the label to produce all of the product identifying information, namely:

a. the warning indicia 26 to consumers not to use the product near heat or an open flame;

b. the instructions indicia 26 to shake well before using;

c. the contents quantity indicia 22, e.g. $\frac{1}{2}$ fl. oz. or 15 ml;

d. the manufacturer or supplier and address (not shown), and e. the particular shade of nail polish identified in words by the indicia which are part of 22 and and by the internal code number on the right side of the label which is represented by reference numeral 29 and is an overprinting of black numerals on a white opaque portion 16 on the front of the label 12 as shown in FIGS. 2 and 3. This printing of the indicia in steps a through d are carried out on the left side of the label behind the boundary which is defined by the inner edge of the opaque white layer 16 shown in FIG. 3. Layer 16 is a white opaque double flood coating at the front side right side of the label and provides the opaque white background for the product code represented by bar code indicia 28 and the numerical indicia alongside the edge of the bar code indicia 28, these numerical indicia being represented by reference numeral 29. In FIG. 2 only a select portion of these numerals are shown and the spacing of the bars in the bar code 28 correlate with certain numbers at the edge of the bars represented by numerical indicia 29. In short, a representative few numbers are shown in FIG. 2 rather than the entire numerical code. The placement of these is best appreciated in the cross-sectional view of FIG. 3 and particularly with relation to the substrate 14 consisting of transparent cellulose acetate, the creation of the boundary at the inner edge of double coated opaque white layer 16 and the relatively thick pressure sensitive coating layer 30.

To better appreciate the thickness of these layers, the indicia 22, 24 and 26 on the left back side of the label have a thickness of about 0.3 to 0.6 mils while the thickness of the white opaque coating 16 is about 1 to 2 mils, these being related to the thickness of the cellulose acetate substrate 14 which varies from about 3 to about 5 mils. The printing of the bar code represented by reference numerals 28 and 29 is significantly greater than the thickness of the product identification indicia above mentioned, e.g. about 0.4 to about 0.8 mils with the result that the combination of black against white resulting from the bar code 28 being overprinted over the opaque layer 16 results in 100% reflection from the white background and the black overprinting.

2. A second operation of printing is necessary for the application of a double flood coat of opaque white, layer 16, at the right side of the label extending from the boundary defined at the inner edge of the lower product printing and extending to the very end of the front of the cellulose acetate pre-cut film 14. This flood coat represented by layer 16 in FIG. 3 is at least twice the thickness and many times as dense in pigment as the pigment density utilized in the back coating of the indicia 22, 24 and 26 on the left side of the label 12. The increase in pigment density and the application of several coats of opaque white pigment provides a completely opaque white background layer 16 in the front 18 of the label in contrast to a translucent indicia background 22, 24 and 26 on the left back side 20 of the label 12.

3. The bar code 28 and the numerical code 29 which are printed on the front 18 of the right side of the label 12 is printed in a highly opaque, dense black pigment which is in a thickness sufficient to provide a highly reflective black area in both the bar indicia and the numerical indicia as is necessary in the binary coding operation as is required for the electronic readings of the label by conventional apparatus of the type shown in Leuck U.S. Pat. No. 3,543,241.

THE APPLICATION OF THE PRESSURE SENSITIVE ADHESIVE

The pressure sensitive adhesive coating 30 is separately applied by conventional methods and machinery after the printing has been carried out. The adhesive may be applied by hot calendering or from solutions in volatile hydrocarbon solvents. The latter procedure is preferred. It is useful to print the back side first in step 1 as indicated above, then to print the front side in two steps by providing a flood coating and the overcoating as indicated in steps 2 and 3 above after which the entire strip in a continuous printing operation is coated on the underside by conventional coating machinery with the pressure sensitive adhesive using a volatile hydrocarbon solvent composition.

Variations in the methods of printing may be used prior to applying the adhesive in which the order of printing steps may be modified or altered in order to fit particular conditions of manufacture. For example, the front side can be printed first in steps 2 and 3, these steps representing the printing of the back side which is described in step 1 above. The important process requirement during printing is that a clear line of demarcation or boundary be observed between the inner line of the back printing and the inner line of the front printing to insure that no back printing extends beneath the white opaque area at the front.

As mentioned in the prior art, pressure sensitive adhesives are widely used for labels as shown in Downing et al, U.S. Pat. No. 4,379,805 and Kennedy, Jr., U.S. Pat. No. 3,420,364. These adhesives can be used with glass but it is not necessary to use special adhesives adapted for plastic containers. A typical pressure sensitive adhesive contains a rubber component which may be natural rubber or synthetic rubber, a tackifier component which is permanently tacky such as an ester of hydrogenated rosin and a stabilizer, and a non-volatile liquid plasticizer such as dibutyl phthalate, tricresyl phosphate or dioctyl phthalate or the like and a hydrocarbon solvent such as heptane. If soft synthetic and tacky polymers are used such as polyvinyl ether polymer, then the plasticizer may be a polyester type plasticizer of an aliphatic polybasic acid such as dioctyl maleate or the like. Light stabilizers, anti-aging compounds (anti-oxidants) and ultraviolet stabilizing agents may be incorporated in order to prevent yellowing of the coating. A typical formulation follows:

A substantially colorless tape was made from the following solution:

Crepe natural rubber: 50 parts
GR-S (X-274): 50 parts
Alkylated polyhydric phenol (stabilizer): 1.0 part
Heptane: 600 parts In the above formula GR-S Rubber is a butadiene styrene copolymer grade especially adapted for blending with milled natural rubber. This synthetic GR-S can be used in the above formula with natural rubber or with reclaimed rubber and is prepared by milling in the cold for a time to give the desired tack and plasticity. It can be used with a small proportion of rosin ester or coumarone-indene resin or with terpene resin together with small amounts of the above mentioned non-volatile liquid plasticizers.

Printing ink compositions are based upon organosol formulations or vinyl paste formulations as shown in Schildknecht "Polymer Processes" Interscience Publishers, 1956 and particularly at pages 623 and 699. Any printing method may be used, e.g. gravure, flexographic, aniline or silk screen as these are defined in Schildknecht at Page 699. The preferred pigment for white is titanium dioxide and for black is carbon black.

Preferred pastes are based on finely dispersed cellulose polymers such as cellulose acetate, cellulose acetate-butyrate and ethyl cellulose. With these dispersed polymers are used non-bolatile liquid plasticizers in a proportion of 2 parts of plasticizer to 1 part of polymer. Examples of liquid plasticizers are dibutyl phthalate, diethyl phthalate, tributyl phosphate, dioctyl phthalate, dibutyl sebacate and acetyl tri-n-butyl citrate.

Among the vinyl pastes, vinyl chloride plastisols or vinyl butyral plastisols may be used. Vinyl butyral is preferred with ethylene glycol and ethyl phthaloly glycolate as the liquid plasticizers.

A small amount of aliphatic alcohol such as n-propanol or n-butanol can be added as a volatile diluent to the paste or organosol.

Nitroethane or nitropropane can be added as a medium boiling solvent to an organosol composition.

A typical formula for white is as follows:

| % by weight | Material |
|---|---|
| WHITE PIGMENT (HEAVY) | |
| 30 | Titanium dioxide |
| 12 | Polyvinyl butyral |
| 30 | Ethylene glycol |
| 18 | Nitro ethane |
| 10 | n-propanol |
| WHITE PIGMENT (LIGHT) | |
| 5 | Titanium Dioxide |
| 12 | Polyvinyl butyrate |
| 40 | Ethylene Glycol |
| 23 | Nitroethane |
| 20 | n-propanol |

A typical black pigment is as follows:

| BLACK PIGMENT | |
|---|---|
| % by weight | Material |
| 12.5 | Carbon Black |
| 12.5 | Polyvinyl butyral |
| 30 | Ethylene glycol |
| 23 | Nitro ethane |
| 20 | n-propanol |

What is claimed is:

1. A transparent gummed label for small nail polish bottles made of glass fitted with a cap applicator comprising:

a precut rectangular transparent cellulose acetate sheet constituting the sole mechanical support of the label, said sheet having top, bottom, left and right edges, said sheet further comprising a major portion and a minor portion, said major portion including said left edge and said minor portion including said right edge, said portions being defined by an imaginary line running between said top and bottom edges, said sheet further comprising a top surface constituting the front surface of the label and an under surface constituting the back surface of the label;

first translucent indicia printed on the under surface of said sheet said first indicia comprising product identifying information and instructions, said first indicia being translucent and confined to the major portion of the under surface of said sheet, to permit seeing therethrough, an opaque printing of substantial thickness, many times greater than the thickness of said first indicia, consisting of an opaque white background coating covering the entire minor portion of said top surface of said sheet, said white coating being overprinted with a bar code and number in dark color and a continuous coating of pressure sensitive adhesive covering the entire under surface of said sheet and applied over said first indicia.

2. A label as claimed in claim 1 in adhesive combination with a clear glass container having a capacity of ½ fluid ounce.

3. A plurality of labels as claimed in claim 1 supported on a peelable backing strip.

4. A label as claimed in claim 1 wherein the thickness of said cellulose acetate sheet is from about 3 to about 5 mils.

5. A label as claimed in claim 4 wherein the thickness of said pressure sensitive adhesive coating on the back of said label is about 1 to 2 mils.

6. A label as claimed in claim 5 wherein the thickness of said first printing on the back of said label is from about 0.3 to about 0.6 mils.

7. A label as claimed in claim 5 wherein the thickness of said opaque white background coating is about 1 to 2 mils.

8. A label as claimed in claim 7 wherein the thickness of the bar code and numerical indicia over said white opaque ground coating is about 0.4 to 0.8 mils.

9. A label for attachment to a transparent container comprising a flexible sheet of transparent base material of a predetermined size and configuration to conform to a portion of the container, the label having first and second adjacent separate portions, the first portion having indicia printed thereon and being substantially transparent to permit the color of the contents of the container to be visually observable through substantially the entire first portion while providing visually readable information for the user, and the second portion being substantially opaque and having opaque indicia imprinted thereon for product identification through the use of optical means.

10. The invention in accordance with claim 9 wherein the first portion is separated from the second portion by a clear line of demarcation so that the portions are in a side-by-side relationship.

11. The invention in accordance with claim 9 wherein the label includes a back surface and a layer of pressure-sensitive adhesive mounted on the back surface thereof so that when the label is applied and flexibly conformed to the outer surface of the container, the adhesive will bond the label to the container in a predetermined fixed position.

12. The invention in accordance with claim 9 wherein the label is rectangular in configuration, the first portion is substantially larger than the second portion and the surface of the container on which the flexible label is applied is cylindrical in shape.

13. The invention in accordance with claim 9 wherein the label is formed of a precut sheet of cellulose acetate material.

14. The invention in accordance with claim 9 wherein the printed indicia of the first portion is formed of a relatively thin layer of white ink and the opaque second portion is formed of a relatively thick underlayer of white ink sufficient to prevent visual observance of the color of the contents of the container therethrough, and wherein the opaque printed indicia of the second portion is formed as an overlayer of black ink on the underlayer of white ink thereby providing the indicia to be read by the optical means.

15. The invention in accordance with claim 9 wherein a plurality of said labels are provided with each label having a predetermined dispersion of adhesive thereon, and the lables being removable mounted on a carrier sheet in a preselected arrangement whereby each label can be selectively removed to expose the adhesive thereon for engagement with the container to affix the label thereon at a predetermined location.

16. The invention in accordance with claim 9 wherein the printed indicia of the first portion is formed of a relatively thin layer of ink of a selected color and the opaque second portion is formed of a relatively thick underlayer of ink of a selected color sufficient to prevent visual observance of the color of the contents of the container therethrough, and wherein the opaque printed indicia of the second portion is formed as an overlayer of ink on the underlayer of ink of a color contrasting to the color of the underlayer thereby providing the indicia to be read by the optical means.

17. A method of forming a label for a transparent container comprising the steps of preforming a flexible sheet of transparent base material having a predetermined size and configuration to conform to a portion of the container, forming a first substantially transparent portion of the label with indicia printed thereon to permit the color of the contents of the container to be visually observable through substantially the entire first portion, and forming a substantially opaque second portion separate from and adjacent to the first portion and having opaque indicia printed thereon for product identification through the use of optical means.

18. The invention in accordance with claim 17 which further comprises the step of positioning the first and second portions in a side-by-side relationship.

19. The invention in accordance with claim 17 which further comprises the step of affixing the label to a substantially cylindrically-shaped nail polish bottle having a preselected shade of nail polish housed therein which is readily observable through the first portion of the label.

20. The invention in accordance with claim 17 which further comprises the step of applying a pressure-sensitive adhesive on the flexible label for bonding the label to the container in a predetermined fixed position when the label is applied to an outer surface of the container.

21. The invention in accordance with claim 17 wherein the step of forming the label includes the step of forming the label in a rectangular configuration; and wherein the steps of forming the first and second portions includes the step of making the first portion substantially larger than the second portion.

22. The invention in accordance with claim 17 wherein the step of forming the label includes the step of making the label from a precut sheet of cellulose acetate material.

23. The invention in accordance with claim 17 which further comprises the steps of applying a relatively thin layer of white ink to a surface of the label situated at the first portion thereof to form the printed indicia of the first portion, and applying a relatively thick underlayer of white ink to a surface of the label situated at the second portion thereof sufficient to prevent visual observance of the color of the contents of the container therethrough and thereafter applying an overlayer of black ink upon the underlayer to provide the indicia to be read by the optical means.

24. The invention in accordance with claim 17 which further comprises the step of affixing the label to a container which is a transparent and glass bottle.

25. The invention in accordance with claim 17 which further comprises the steps of forming a plurality of said labels with each label having a predetermined dispersion of adhesive thereon, and removably mounting the plurality of labels on a carrier sheet in a preselected arrangement whereby each label can be selectively removed to expose the adhesive thereon for engagement with the container to affix the label thereon in a predetermined location.

26. The invention in accordance with claim 17 which further comprises the step of applying a relatively thin layer of ink of a selected color to the sheet of base material to form the printed indicia of the first portion, and applying a relatively thick underlayer of ink of a selected color to the sheet of base material in a sufficient amount to prevent visual observance of the color of the contents of the container therethrough, and thereafter applying an overlayer of ink of a color contrasting to the color of the underlayer upon the underlayer thereby providing the indicia to be read by the optical means.

* * * * *